United States Patent [19]

Packer et al.

[11] Patent Number: 4,783,341

[45] Date of Patent: Nov. 8, 1988

[54] METHOD AND APPARATUS FOR MEASURING THE DENSITY AND HARDNESS OF POROUS PLASMA SPRAYED COATINGS

[75] Inventors: Louis L. Packer, Enfield; Glenn T. Janowsky, Coventry, both of Conn.

[73] Assignee: United Technologies Corporation, Hartford, Conn.

[21] Appl. No.: 45,341

[22] Filed: May 4, 1987

[51] Int. Cl.⁴ .................................................. B05D 1/10
[52] U.S. Cl. ....................................... 427/8; 427/423; 378/54; 73/32 R; 73/150 R
[58] Field of Search ............... 73/32 R, 150 R; 427/8, 427/423; 378/54, 55

[56] References Cited

U.S. PATENT DOCUMENTS

| | | | |
|---|---|---|---|
| 3,046,402 | 7/1962 | Cherry | 378/54 |
| 4,284,658 | 8/1981 | Davis et al. | 427/423 X |
| 4,336,276 | 6/1982 | Bill et al. | 427/34 |
| 4,386,112 | 5/1983 | Eaton | 427/34 |
| 4,405,284 | 9/1983 | Albrecht | 427/423 X |
| 4,618,975 | 10/1986 | Glantschnig | 378/54 X |

FOREIGN PATENT DOCUMENTS

59-166885  9/1984  Japan ...................................... 378/54

OTHER PUBLICATIONS

"Radioisotope Applications Engineering", Jerome Kohl et al., 1961, pp. 461, 478-486.

*Primary Examiner*—Shrive P. Beck
*Attorney, Agent, or Firm*—James M. Rashid

[57] ABSTRACT

This invention relates to a method for making porous metal plasma sprayed abradable seals. Radiation transmission techniques are utilized to determine the as-sprayed density of a deposit containing metal and polymer powder particles. Based on the measuring density, a mathematical prediction is made of what the surface hardness of the sprayed deposit will be after it has been machined and then heated to remove the polymer powder particles. If the predicted hardness is outside of the desired range, changes are made in the plasma spray parameters.

7 Claims, 1 Drawing Sheet

METHOD AND APPARATUS FOR MEASURING THE DENSITY AND HARDNESS OF POROUS PLASMA SPRAYED COATINGS

TECHNICAL FIELD

The technical field which this invention pertains to is the measurement of the density and hardness of porous plasma sprayed coatings.

BACKGROUND

Plasma sprayed coatings (i.e., flame, arc, and other similar sprayed coatings) are commonly used in gas turbine engines and other types of turbomachinery. One reason for their widespread use is that the process for applying plasma sprayed coatings is capable of depositing a wide variety of coating compositions onto a substrate.

Porous metal abradable seals (also referred to as abradable coatings) may be applied to a substrate by simultaneously plasma spraying metal and polymer particles onto the substrate, generally in accordance with U.S. Pat. No. 3,723,165 to Longo, and copending and commonly assigned U S. Pat. Nos. 4,696,855 to Pettit et al and 4,664,973 to Otfinoski et al, the disclosures of which are all incorporated by reference. For optimum operating characteristics, the abradable coating needs a precisely controlled combination of properties. Tests have indicated that the density and hardness of the coating are among the most important properties, since they correlate well with seal performance during service use.

Accordingly, researchers have expended considerable efforts to develop improved methods for making abradable seals, and to develop methods for measuring the density and hardness of sprayed abradable seals. The present invention satisfies these needs.

SUMMARY OF THE INVENTION

According to this invention, the density and hardness of a porous, plasma sprayed abradable seal are measured by gamma radiation transmission techniques. The seal preferably comprises a dense metal bondcoat layer applied directly to a substrate, and a porous metal layer applied over the bondcoat. Both layers are applied by plasma spray techniques. The porosity of the outer layer gives the seal its desired abradability.

The bondcoat is applied by conventional plasma spray techniques. The porous layer is made by simultaneously spraying metal and polymer powder particles onto the bondcoat, machining the seal to its desired configuration, and then heating the seal to thermally decompose (volatilize) the polymer, whereby a porous layer is formed.

Using gamma radiation transmission techniques, the density of the outer layer in the as-sprayed condition (i.e., the layer prior to machining or heating) is measured, and then a calculation made to convert the as-sprayed seal density to the fully processed (i.e., machined and heated) seal hardness. These measurements are quick, reproducible, and allow for timely adjustments to be made of the spray parameters, if necessary.

In particular, a known amount of gamma radiation is passed from a radiation source, through the substrate, and into a radiation detector at various intervals during the plasma spray process. The thickness of the sprayed layers is also measured during the same intervals. Based on these measurements, and knowing the amount of radiation which the coated substrate absorbs, a calculation of seal density is made. An additional calculation converts this as-sprayed seal density to the fully processed seal hardness.

The seal density and hardness are indicative of how the seal will perform during service use. If these properties are not within the desired ranges, modifications of the plasma spray parameters are made to produce seals having the desired density and hardness.

BEST MODE FOR CARRYING OUT THE INVENTION

This invention will be described with reference to the plasma spray deposition of a porous metal abradable seal onto a gas turbine engine component. However, it should be recognized that the invention will be useful in the fabrication and characterization of other types of porous (i.e., less than 100% dense) coatings.

The preferred abradable seal (also referred to as a coating or a deposit) is preferably characterized by a homogenous mixture of metal and polymer powders. If desired, the spray parameters may be modified so that the ratio of metal to polymer powder in the deposit varies with the thickness of the deposit. Such a coating would be considered to have a graded microstructure.

The preferred abradable coating system contains metal and polymer powder particles, where the metal particles are selected from a group consisting of MCr, MCrAl, MCrAlY, and refractory modified MCrAlY, where M is nickel, cobalt, iron, or mixtures thereof. The polymer powder used in the preferred abradable coating system is a decomposable organic polymer; polyester and polymethyl methacrylate are useful.

To enhance the strength of the bond between the abradable coating and the metal substrate to which it is applied, a thin bondcoating is first applied to the surface of the substrate. The bondcoating is applied so that it intentionally has a rough surface texture, to enhance the bond between it and the abradable coating applied thereover. The bondcoating may be a plasma sprayed MCr, MCrAl, MCrAlY, or refractory modified MCrAlY.

Figure 1:
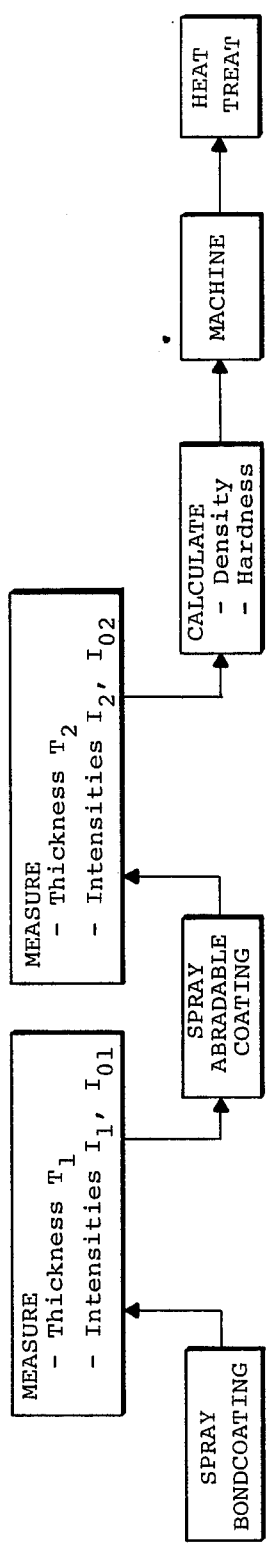
FIG. 1 is a flow chart showing the method for fabricating the sprayed abradable seal according to the invention.
Figure 2:
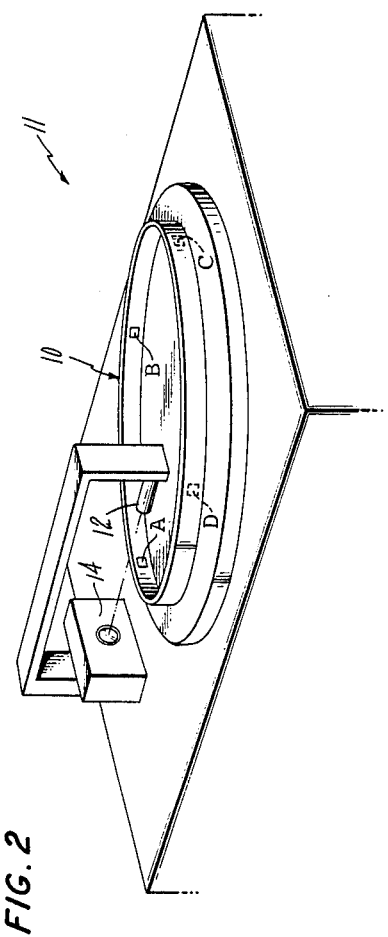
FIG. 2 is a schematic diagram of an apparatus useful for measuring density and hardness using transmission radiation emission according to this invention.

The steps in producing an abradable seal according to this invention are shown in FIG. 1. The first step is to apply the bondcoating to the seal substrate. Then, the bondcoated substrate is assembled between a radiation transmission apparatus 11 such as is shown schematically in FIG. 2. In FIG. 2, the substrate to which the seal is applied is identified by reference numeral 10. A typical gas turbine engine substrate coated according to this invention is an annular compressor stator.

The radiation transmission apparatus 11 comprises a radiation source 12 and a radiation detector 14. A preferred source of radiation in the source 12 is the gadolinium 153 isotope; it has a specific activity of about 110 curies/cubic centimeter and an energy level of about $10^5$ electron volts. Other radioactive isotopes may also be used, e.g., americium 241 or barium 133. The particular choice of isotope will depend primarily on the combined thickness of the substrate and the abradable coating applied thereto. The radiation detector 14 includes signal processing electronics necessary to convert the radiation which impinges upon it into a quantitative output signal such as output voltage.

After the bondcoating has been applied to the stator 10, the stator 10 is positioned between the radiation source 12 and the radiation detector 14 so that when the source 12 emits a beam of radiation, the beam passes through a known location on the coated stator 10 (the location designated "A" in FIG. 2). All subsequent emissions of radiation and measurements of coating thickness (described below) which will be used to characterize the coating at this point on the substrate 10 must be conducted through the same location A. To obtain a representative measurement of the seal density and hardness, at least three other locations (identified as B, C, and D in the Figure) should be characterized.

Energy which passes through the stator 10 at location A and into the detector 14, is measured as an output voltage $I_{1A}$. (Some of the radiation is absorbed by the bondcoating and by the stator 10.) The stator is then indexed to locations B, C, and D and the output voltages $I_{1B}$, $I_{1C}$, $I_{1D}$, respectively, are measured. The bondcoated stator 10 is then removed from the fixture and a known quantity of gamma radiation is directed, in open air, from the source 12 to the detector 14. (Measurements "in open air" are made while the stator is removed from between the radiation source 12 and detector 14.) This open air measurement, $I_{01}$, is made to account for the decay of the radioactive isotope between the time that the transmission measurements are made of the bondcoated stator and the time that transmission measurements are made of the stator with the abradable layer applied (discussed below). Precise measurements of the coated substrate thickness (i.e., the combined thickness of the stator and bondcoat) are also made at the known locations A, B, C, and D and are identified as $T_{1A}$, $T_{1B}$, $T_{1C}$, and $T_{1D}$, respectively.

The next step in the invention process is to apply the abradable layer to the surface of the bondcoating. The completely coated stator 10 is then assembled into the radiation measurement fixture, and the amount of radiation which penetrates the stator 10 at the known locations A, B, C, and D is measured as described above and identified as $I_{2A}$, $I_{2B}$, $I_{2C}$, and $I_{2D}$ respectively. The completely coated stator is then removed from its fixture and the output voltage $I_{02}$ is measured in open air. The total thickness of the substrate at locations A, B, C, and D is also measured, and identified as $T_{2A}$, $T_{2B}$, $T_{2C}$, and $T_{2D}$.

The density of the abradable layer is calculated at each of the four locations A, B, C, D to determine whether there are any significant density variations about the seal circumference. These four densities are then averaged to obtain an overall seal density. The formula used to calculate the density at, e.g., location A, is:

$$\rho_A = 1/\mu \{\log_e[(I_{02} \times I_{1A})/(I_{01} \times I_{2A})]/(T_{2A} - T_{1A})\}$$

where $\mu$ is the absorption coefficient of the abradable layer. The seal density at locations B, C, and D is calculated in a similar fashion.

The coefficient $\mu$ is determined in the following manner: First the density of a statistically significant number of free-standing abradable layers (i.e., excluding substrate and bondcoat) having varying densities is measured. This may be done, e.g., in accordance with ASTM specification C20-80a. Then the free-standing abradable layers are subjected to transmission radiation measurements similar to those described above: The intensity of the detected intensity through each seal "n" is measured ($I_n$), as is the intensity in open air ($I_o$). Then, the quantity $[\log_e(I_o/I_n)]/T_n$ is calculated, where $T_n$ is the thickness of each layer n. This calculated quantity for each layer is its gage response. When gage response for each layer is plotted linearly as a function of that layer's measured density, the slope of the line is the absorption coefficient $\mu$.

The absorption coefficient may also be calculated analytically. By knowing the composition of the powder which is sprayed to make the layer, the absorption coefficient is calculated as follows:

$$\mu = \sum_{i=1}^{n} (a_i \times \mu_i)$$

for a powder composition which consists of n elements and where $a_i$ is the compositional weight percent of each element in the powder and $\mu_i$ is the absorption coefficient of each element. (Elemental absorption coefficients are listed in, e.g., "Compilation of X-Ray Cross Sections", W. H. McMaster, National Technical Information Services, January 1970.) The calculated absorption coefficient agrees well with that derived by the method described above.

A laboratory program and t-test statistical analysis revealed that the as-sprayed seal density, determined according to this invention, was proportional to the hardness of the fully processed seal (i.e., after machining and heating to remove the polymer powder particles). This was true even though density is a bulk density of the as-sprayed abradable coating and hardness is a measurement of the surface condition of the fully processed abradable coating. The proportionality factor which relates density and hardness is identified as A, and varies according to the specific powders sprayed and processing techniques utilized. The factor A is readily determined using conventional statistical analysis. Therefore, according to this invention, to relate the transmission radiation measured as-sprayed density to the expected surface hardness of the fully processed seal, the seal density $\rho$ is multiplied by the proportionality factor A.

Tests have shown that the surface hardness of the fully processed seal is an accurate indicator of the abradability of the seal. For the preferred refractory modified MCrAlY and polymethyl methacrylate deposit, the desired hardness of the fully processed seal is in the range of about 50 to 75 on the Rockwell 10Z scale.

After the seal has been sprayed, the density and hardness are calculated as described above. If the density and hardness are outside of the required ranges, modifications of the spray parameters can be made immediately, before any other engine components are sprayed. Only if the density and hardness are within the required ranges is the coated component subjected to post-coating processing, which comprises first, machining the seal to the desired thickness. Machining techniques that would compress the surface of the seal, or cause the surface to be smeared over rather than machined away, should not be used. After machining, the seal is heated in a protective atmosphere to thermally decompose the polymer powder. Preferably, the powder is completely volatilized when heated, so that no residue of the polymer is left behind. Such residue would likely impact upon the abradability of the seal. As a result of the heating process, a porous metal abradable seal is produced, and the stator is ready for service.

Use of the invention has resulted in a significant improvement in the yield of sprayed abradable seals. Prior to the invention, the yield of seals within the target ranges of density and hardness was slightly greater than about 50%. After the invention technique was implemented, the yield of acceptable seals rose considerably. The increase in yield is primarily due to the ability to obtain timely measurements of density and hardness, and to adjust spray parameters, if necessary, in response to these measurements. Prior to the invention, hardness was only measurable after the coating was machined and the polymer particles were volatilized from the seal. Typically, these process steps did not take place until several days following the time the seal had actually been sprayed. If the spray parameters were incorrect (i.e., produced seals outside of the target property ranges) several seals were sprayed in the interim before the parameters could be modified. This invention allows the seal properties to be measured immediately after the seal is sprayed, and if necessary, modifications in the spray parameters can be made before any more seals are sprayed.

The determination of density and hardness can be performed without moving the component being coated from a fixturing apparatus dedicated solely to spraying to another apparatus dedicated solely to gamma transmission measurements. In the particular case of the plasma spray application of a bondcoating and abradable layer onto an annular compressor stator 10, such as is shown in FIG. 2, the stator is rotated in front of a plasma spray gun as powder is sprayed onto the stator. When the full thickness of bondcoat and abradable layer have each been applied, and while the stator is still rotating, the thicknesses $T_1$ and $T_2$, respectively, are determined using noncontacting techniques such as laser triangulation. Also, while the stator is rotating, the intensities $I_1$ and $I_2$, are measured. By measuring thickness and intensity while the stator is rotating, rather than measuring these quantities at a limited number of discrete locations while the stator is stationary, a more precise calculation of density and hardness is made. Furthermore, these measurements can be imputed directly into a computer which can, if necessary, adjust the spray parameters to achieve the desired combination of properties in the seal being fabricated.

Although the invention has been shown and described with respect to a preferred embodiment, it should be understood that various other changes and omissions may be made without departing from the spirit and scope of the invention. This invention is useful in measuring the density and hardness of many porous materials. The material need not necessarily be plasma sprayed, nor need it be a plasma sprayed abradable seal which includes a bondcoat. If, for example, a porous metal deposit does not include a bondcoat, the same measurments and calculations described above are made; however, the quantities $I_1$ and $T_1$ are measured prior to the application of the powder used to make the porous metal deposit.

While this invention has been described with reference to the plasma spraying of metal and polymer powder particles to produce a homogenous deposit, ceramic powder particles may also be sprayed, and the sprayed deposit may contain any combinations of these different powder types. The powders may be sprayed to produce homogenous or graded deposits. Other modifications may be made which are still within the scope of the invention.

We claim:

1. A method for fabricating an annular component having a porous metal abradable seal thereon and for measuring the surface hardness of the seal, comprising the steps of rotating the component relative to a sprayed stream of metal and polymer powder particles, wherein the metal and polymer powder particles are deposited onto the surface of the component; heating the metal and polymer power deposit to remove the polymer particles therefrom to form a porous metal abradable seal; and prior to said heating step, measuring the surface hardness of the porous metal abradable seal using gamma radiation transmission techniques.

2. The method of claim 1, wherein the gamma transmission measurements are made while the component is stationary.

3. The method of claim 1, wherein the gamma transmission measurements are made while the component is rotating.

4. A method for applying a sprayed metal coating onto a substrate and measuring the surface hardness of the coating, the coating comprising a sprayed metal bondcoat on the surface of the substrate and a sprayed metal abradable coating on the surface of the bondcoat, wherein said hardness is the hardness of the abradable coating, the method comprising the steps of:

(a) spraying the bondcoat onto the surface of the substrate and measuring the combined thickness $T_1$, of the substrate and bondcoat in a known location;

(b) directing gamma radiation from a radiation source through said known location on the bondcoated substrate to a radiation detector, and measuring the amount of radiation $I_1$, received by the detector;

(c) directing radiation in open air from the source to the detector, and measuring the amount of radiation, $I_{01}$, received by the detector;

(d) spraying the abradable coating onto the surface of the bondcoat and measuring the combined thickness, $T_2$, of the substrate, bondcoat, and abradable coating in said known location;

(e) directing radiation from the radiation source through said known location on the substrate coated in step (d) and to the radiation detector, and measuring the amount of radiation, $I_2$, received by the detector;

(f) directing radiation in open air from the source to the detector, and measuring the amount of radiation, $I_{02}$, received by the detector; and (g) calculating the surface hardness of the abradable coating by the formula $$H = A\rho$$

where $$\rho = 1/\mu \{ \log_e [(I_{02} \times I_1)/(I_{01} \times I_2)]/(T_2 - T_1) \}$$

and $H$ = surface hardness of the abradable coating
$\rho$ = density of the abradable coating
$A$ = statistically determined proportionality factor between surface hardness and density $\mu$ = absorption coefficient of the abradable coating.

5. The method of claim 4, wherein the step of spraying the abradable coating comprises the steps of simultaneously spraying metal and polymer powder particles onto the surface of the bondcoating to form an abradable coating, and then heating the abradable coating to remove the polymer powder particles to make a porous metal abradable seal, wherein the quantity H is a measurement of the surface hardness of the porous metal abradable seal, and the quantity $\rho$ is a measurement of the density of the as sprayed abradable coating.

6. The method of claim 4, wherein the substrate is annular in shape, and further comprising the steps of plasma spraying the bondcoating and abradable coating onto the substrate while the substrate is rotating, and measuring the thicknes $T_1$ and $T_2$ and intensities $I_1$ and $I_2$ while the substrate is rotating.

7. A method for applying a sprayed metal coating onto a substrate and for measuring the surface hardness of the coating, the coating comprising a sprayed metal bondcoat on the surface of the substrate and a sprayed metal abradable coating on the surface of the bondcoat, wherein said abradable coating is porous metal and wherein said hardness is the hardness of the porous metal abradable coating, the method comprising the steps of:

(a) spraying metal powder particles onto the surface of the substrate to form the bondcoat, and measuring the combined thickness $T_1$, of the substrate and bondcoat in a known location;

(b) directing gamma radiation from a radiation source through said known location on the bondcoated substrate to a radiation detector, and measuring the amount of radiation $I_1$, received by the detector;

(c) directing radiation in the open air from the source to the detector, and measuring the amount of radiation, $I_{01}$, received by the detector;

(d) spraying metal and polymer particles onto the surface of the bondcoat to form a coating layer containing metal and polymer, and measuring the combined thickness, $T_2$, of the substrate, bondcoat, and the metal and polymer layer in said known location;

(e) directing radiation from the radiation source through said known location on the substrate coated in step (d) and to the radiation detector, and measuring the amount of radiation, $I_2$, received by the detector;

(f) directing radiation in open air from the source to the detector, and measuring the amount of radiation, $I_{02}$, received by the detector;

(g) heating the coated substrate to remove the polymer from said metal and polymer layer to make a porous metal abradable coating; and (h) prior to said step of heating, calculating the surface hardness of the porous metal abradable coating by the formula $H = A\rho$ where $\rho = 1/\mu\{\log_e[(I_{02} \times I_1)/(I_{01} \times I_2)]/(T_2 - T_1)\}$ and H = surface hardness of the porous metal aradable coating
$\rho$ = density of the metal and polymer layer
A = statistically determined proportionality factor between surface hardness and density
$\mu$ = absorption coefficient of the metal and polymer abradable coating.

* * * * *

UNITED STATES PATENT AND TRADEMARK OFFICE
CERTIFICATE OF CORRECTION

PATENT NO. : 4,783,341

DATED : November 8, 1988

INVENTOR(S) : Louis L. Packer et al.

It is certified that error appears in the above-identified patent and that said Letters Patent is hereby corrected as shown below:

In the ABSTRACT, line 5, "measuring" should read -- measured --.

Column 6, line 14, "power" should read -- powder --.

Signed and Sealed this

Nineteenth Day of December, 1989

Attest:

JEFFREY M. SAMUELS

Attesting Officer     Acting Commissioner of Patents and Trademarks